(12) United States Patent
Helly et al.

(10) Patent No.: US 6,444,013 B1
(45) Date of Patent: Sep. 3, 2002

(54) PURIFICATION OF METHYLSILANES

(75) Inventors: Patrick J. Helly, Valley Center, CA (US); Masud Akhtar, Lawrenceville, NJ (US)

(73) Assignee: The Boc Group, Inc., Murray Hill, NJ (US)

( * ) Notice: Subject to any disclaimer, the term of this patent is extended or adjusted under 35 U.S.C. 154(b) by 0 days.

(21) Appl. No.: 09/664,627

(22) Filed: Sep. 19, 2000

(51) Int. Cl.[7] ................................................ B01D 53/02
(52) U.S. Cl. ............................. 95/116; 95/139; 95/141
(58) Field of Search ............................... 96/108; 95/114, 95/115, 116, 141, 143, 90, 95, 139

(56) References Cited

U.S. PATENT DOCUMENTS

| | | | |
|---|---|---|---|
| 4,099,936 A | * | 7/1978 | Tarancon |
| 4,224,040 A | * | 9/1980 | Gazzarrini et al. |
| 4,461,908 A | | 7/1984 | Takamizawa et al. |
| 4,554,141 A | * | 11/1985 | Scull et al. |
| 4,774,347 A | | 9/1988 | Marko et al. |
| 4,976,944 A | * | 12/1990 | Pacaud et al. |
| 4,985,580 A | | 1/1991 | Chadwick et al. |
| 5,051,117 A | * | 9/1991 | Prigge et al. |
| 5,206,004 A | * | 4/1993 | Park |
| 5,290,342 A | * | 3/1994 | Wikman et al. |
| 5,493,042 A | | 2/1996 | Ault et al. |
| 5,493,043 A | | 2/1996 | Marko et al. |
| 5,916,245 A | * | 6/1999 | Tom |
| 5,961,695 A | * | 10/1999 | Hasegawa et al. |
| 5,980,608 A | * | 11/1999 | Dietz et al. |
| 6,027,547 A | * | 2/2000 | Tom et al. |

FOREIGN PATENT DOCUMENTS

EP  0 812 849 A2  12/1997

OTHER PUBLICATIONS

Masud Akhtar, "Preparation of Ultra–High Purity Higher Silanes and Germanes," SYNTH. REACT. INORG. MET.–ORG. CHEM., 16(5), 729–748 (1986).

* cited by examiner

*Primary Examiner*—Duane S. Smith
(74) *Attorney, Agent, or Firm*—Ira Lee Zebrak; Salvatore P. Pace

(57) ABSTRACT

A process for purifying methylsilane is described. Methylsilane containing impurities such as carbon dioxide, chlorosilane and atmospheric gases is fed from a source container unit to an adsorption unit at −40° C. The adsorption unit is connected to a collection unit at −190° C. where the purified methylsilane is transported and can be stored.

14 Claims, 1 Drawing Sheet

PURIFICATION OF METHYLSILANES

FIELD OF THE INVENTION

The present invention relates to processes for purifying methylsilane. More particularly, the present invention provides for purifying and condensing methylsilane gas through cryogenic adsorption techniques.

BACKGROUND OF THE INVENTION

Organosilicon gases, particularly methylsilane are employed in the semiconductor industry as coatings and films. A typical process for producing methylsilanes is called the "direct process." This is the reaction of methyl chloride and silicon in the presence of a copper catalyst. The effluent from the reactor, however, is still a mixture of methylsilanes and high boiling materials such as disilanes, polysiloxanes, silylmethylenes and the like. This effluent must then be distilled to separate the methylsilane from the other silanes present.

Additionally, these synthesis methods also result in the generation of olefinic and chlorinated hydrocarbons. These individual species can cause separation problems with the above-mentioned distillation process, as well as problems relating to color and stability of the resulting product.

A typical sample of methylsilane gas may find various impurities in it that can interfere with the use of methylsilane in semiconductor fabrication and processing. These impurities include for example hydrogen, nitrogen, argon, oxygen, methane, ethane, carbon dioxide, silane, chlorosilane and dimethylsilane.

Applicants have discovered that the use of a cryoadsorption process will remove impurities, particularly chlorosilanes and carbon dioxide, better than processes such as distillation.

SUMMARY OF THE INVENTION

The present invention provides for a process for the purification of methylsilane. The process provides for the steps of providing a source of methylsilane containing impurities, directing the methylsilane to an adsorption vessel for adsorption and degassing and directing the purified methylsilane to a collection vessel.

The adsorption vessel will contain an appropriate adsorbent such as magnesium silicate and will be kept at a temperature of about −40° C.

The impurities typically found in methylsilane gas are hydrogen, nitrogen, argon, oxygen, methane, ethane, carbon dioxide, silane, chlorosilane and dimethylsilane.

DETAILED DESCRIPTION OF THE INVENTION

Figure 1:
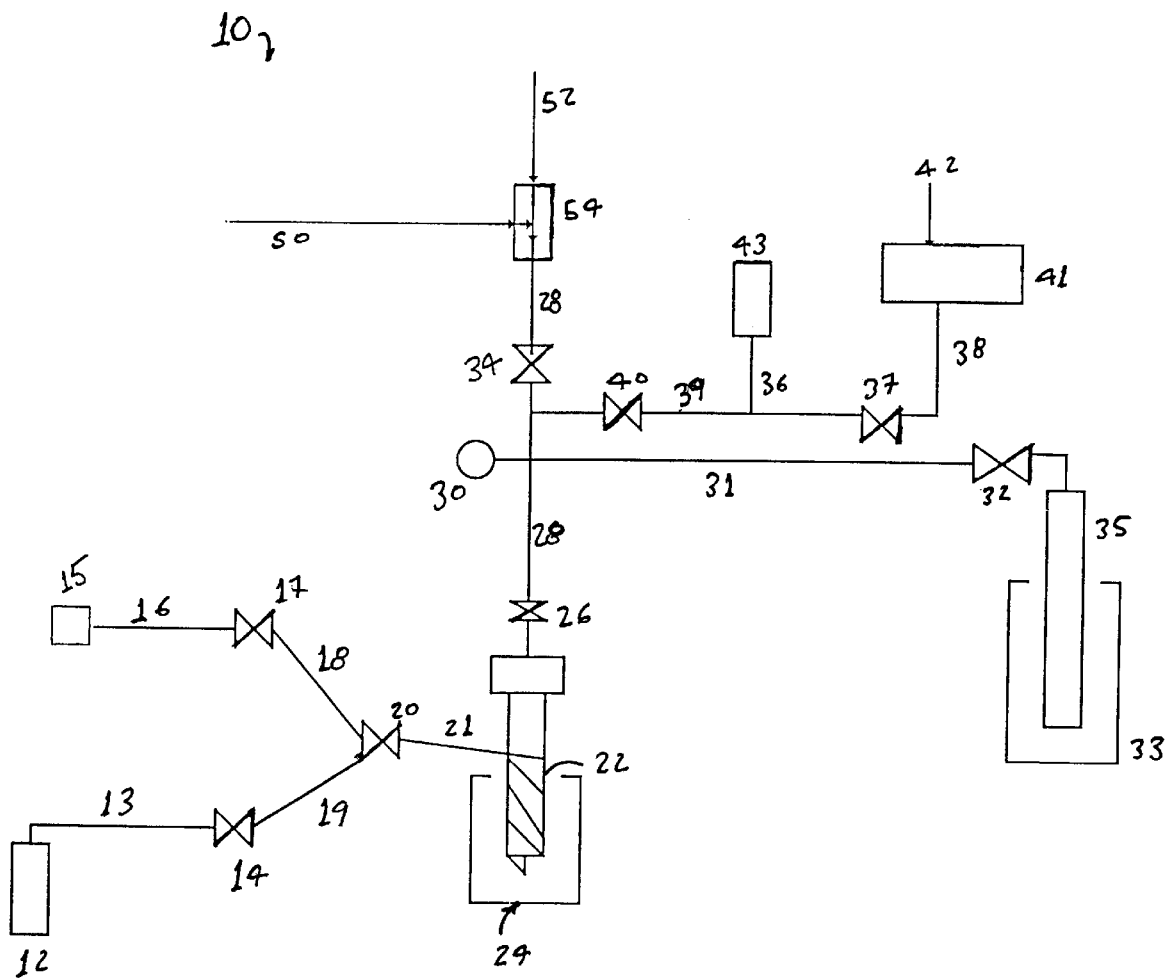
FIG. 1 is a schematic representation of the system used to purify methylsilane.

FIG. 1 is a schematic representation of the overall purifying system 10. Vessel 12 contains the methylsilane that is to be purified. Typically, it is a cylinder and valve arrangement which attaches to line 13 and connects via 13 to an isolation valve 14.

Helium is supplied to the system from container 15. The helium can be any grade that will effectively aid in purging the system, such as grade 6. The container 15 is typically a cylinder and regulator which connects to an inlet valve 17 via line 16. Lines 18 and 19 connect valves 17 and 14 respectively to valve 20 which is the inlet valve to the adsorption unit 22.

The inlet valve 20 attaches to adsorption unit 22 via a line 21. The line can prior to connecting to the unit. The adsorption unit 22 is typically fashioned from stainless steel and will contain an appropriate adsorbent. Representative examples include but are not limited to magnesium silicate which is available from Aldridge Chemicals as Florosil, alumina, silica gel, molecular sieves and zeolites. The absorption unit is kept at a temperature ranging from about −20° C. to about −40° C., with a temperature of −40° C. preferred, by a container 24. The container is typically a stainless steel dewar capable of holding liquid nitrogen.

Line 28 connects the adsorption unit with an outlet isolation valve 26 to line 31 which is attached to a pressure gauge 30. The purified methylsilane will travel through line 28 to line 31 to an isolation valve 32 which connects to the methylsilane receiver unit 35. This unit is typically a cylinder which is capable of containing gas. The receiver unit is within a stainless steel container 33 capable of holding liquid nitrogen. The receiver unit is typically held at a temperature ranging from about −170° C. to about −190° C. with a temperature of about −190° C. preferred.

Line 28 further connects to line 39 and further connects to line 36 through valve 40. Line 36 connects with a capacitance manometer vacuum gauge. Line 39 continues through a high vacuum isolation valve 37 to line 38 which attaches to a vacuum system 41. The vacuum system is a turbo molecular vacuum pump/diaphragm backing pump system which is vented through line 42.

Line 28 further connects to a vacuum venturi isolation valve 34 which leads to a vacuum venturi 54 which utilizes nitrogen gas which is delivered through line 52. Line 50 connects a scrubber system to the venturi.

Typically, the components of this system are made of a material that can be manipulated and shaped and can withstand the somewhat large changes in temperature that the system undergoes. This material may be stainless steel, but could also be glass in portions.

In one embodiment of the present invention, the system as described above and in FIG. 1 is first checked for vacuum integrity. In step 1, all valves 14, 17, 20, 26, 30, 32, 34, 40 and 37 are closed, the vacuum system is started and allowed to work up for 30 minutes. Valve 37 is opened in step 2 and the capacitance manometer meter 43 is turned on. The meter is allowed to warm up for 30 minutes in step 3.

In step 4, the source cylinder of methylsilane 12 is attached with its valve closed to the manifold valve 14. The helium cylinder 15 with its valve closed is attached to valve 17 in step 5. The receiver cylinder 35 is attached to manifold valve 32 and the cylinder is opened in step 6. After 30 minutes, step 7 is performed by opening valves 40, 26, 20, 17 and 19 while keeping valve 34 closed. Step 8 is to allow the manifold system to evacuate to a stable pressure reading. In step 9, valve 37 is closed and the manometer meter 43 checked for leaks. Lastly, in step 10, the entire system 10 is purged 10 times with grade 6 helium to 100 psig, held at pressure for 30 minutes, followed by vacuum evacuation to a low-pressure stable reading.

Once the system has been satisfactorily purged and evacuated, the purification procedure may begin. First, the source cylinder 12 is cooled to −40° C. using a delimonene/dry ice bath, in a stainless steel dewar. Next, the adsorber vessel 22 is cooled to −40° C. with a delimonene/dry ice bath in a stainless steel dewar 24. The receiver cylinder 35 is then cooled to −190° C. using liquid nitrogen in a stainless steel dewar 33. All temperature measurements were made using a thermocouple and meter which are not illustrated in FIG. 1.

Step 4 ensures the vacuum integrity of the manifold system by opening valves 14, 40 and 37 while keeping the source cylinder 12 and valves 17 and 34 closed. Next, valves 40 and 37 are closed and the source cylinder slowly opened up with its pressure measured at 30.

Boiling of the liquid nitrogen is an indication that gas is flowing from the source cylinder through the adsorption vessel and collecting in the receiver cylinder. When the boiling has stopped, the cooling bath is removed from the source cylinder and the cylinder is allowed to warm to room temperature. The source cylinder is then warmed with, for example, a heat gun until there is no observable liquid nitrogen boiling in the receiver cylinder.

At this stage, the purification transfer is complete and shutdown is performed. Valve 32 is closed, the line to nitrogen dewar is removed, the source cylinder is closed and valve 34 is opened allowing the manifold to vent to the scrubber through line 50. Once the receiver cylinder has warmed to room temperature, valve 32 is closed and the receiver cylinder removed and forwarded for analysis. The entire system can then be purged and evacuated as described above.

The above procedure was performed on a commercially available sample of methylsilane. The sample as received had the following impurities as determined through gas chromatography measurement as shown in Table I.

TABLE I

| Component | Amount (ppm) |
| --- | --- |
| Hydrogen | 50 |
| Nitrogen | 0.70 |
| Ar and $O_2$ | <0.5 |
| Methane | 0.13 |
| Ethane | 0.96 |
| Carbon Dioxide | 1.92 |
| Silane | <0.5 |
| Chlorosilane | 6.5 |
| Dimethylsilane | — |

After running the purification process once, the sample of methylsilane had the following levels of contaminants as shown in Table II.

TABLE II

| Component | Amount (ppm) |
| --- | --- |
| Hydrogen | 8 |
| Ar and $O_2$ | <0.1DL |
| Carbon Dioxide | <0.1DL |
| Chlorosilane | <0.5DL |
| Nitrogen | <0.1DL |
| Methane | <0.1DL |
| Ethane | <0.2DL |
| Silane | <0.5DL |

As can be seen, only one residual contaminant was in higher than trace amounts after the purification process.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

Having thus described the invention, what we claim is:

1. A process for removing impurities from methylsilane comprising the steps of providing a source of methylsilane containing impurities; adding said methylsilane to an adsorption unit; and collecting the purified methylsilane in a collection unit.

2. The process as claimed in claim 1 wherein said adsorption unit contains an adsorbent selected from the group consisting of magnesium silicate, alumina, silica gel, molecular sieves, and zeolites.

3. The process as claimed in claim 1 wherein said impurities are selected from the group consisting of hydrogen, nitrogen, argon, oxygen, methane, ethane, carbon dioxide, silane, chlorosilane and dimethylsilane.

4. The process as claimed in clam 1 wherein said source of methylsilane and said adsorption unit are at a temperature of −40° C.

5. The process as claimed in clam 1 wherein said collection unit is at a temperature of about −170° C. to −190° C.

6. The process as claimed in clam 1 wherein said source of methylsilane is a cylinder.

7. The process as claimed in clam 1 wherein said collection unit is a cylinder.

8. A process for the purification of methylsilane comprising adding methylsilane containing impurities to an adsorption unit containing an adsorbent.

9. The process as claimed in claim 8 wherein said adsorbent is selected from the group consisting of magnesium silicate, alumina, silica gel, molecular sieves, and zeolites.

10. The process as claimed in claim 8 wherein said impurities are selected from the group consisting of hydrogen, nitrogen, argon, oxygen, methane, ethane, carbon dioxide, silane, chlorosilane and dimethylsilane.

11. The process as claimed in claim 8 wherein said adsorption unit is at a temperature of about −20° to −40° C.

12. The process as claimed in claim 10 wherein said impurity is selected from the group consisting of carbon dioxide and chlorosilane.

13. The process as claimed in claim 8 wherein said methylsilane containing impurities is formed by reacting methyl chloride and silicon in the presence of a copper catalyst.

14. The process as claimed in claim 8 wherein said adsorption unit is purged with helium gas prior to introducing said methylsilane.

* * * * *